United States Patent [19]

Wicher

[11] Patent Number: 5,068,356

[45] Date of Patent: Nov. 26, 1991

[54] HINDERED PHENOLIC N-(AMIDO)IMIDES

[75] Inventor: Jerome Wicher, West Seneca, N.Y.

[73] Assignee: Atochem North America, Inc., Philadelphia, Pa.

[21] Appl. No.: 481,940

[22] Filed: Feb. 20, 1990

[51] Int. Cl.$^5$ .................. C07D 209/56; C07D 209/46; C07D 207/408; C07D 207/448

[52] U.S. Cl. .................................... 548/546; 548/548; 548/477; 548/435

[58] Field of Search .................. 548/548, 546, 477; 59/435

[56] References Cited

U.S. PATENT DOCUMENTS

| | | | |
|---|---|---|---|
| 3,706,798 | 12/1972 | Dunnenberger et al. | 564/163 |
| 3,734,884 | 5/1973 | Dunnenberger et al. | 260/4 |
| 3,888,824 | 6/1975 | Dexter | 524/194 |
| 3,933,736 | 1/1976 | Yoshikawa et al. | 260/458 |
| 3,956,331 | 5/1976 | Yoshikawa et al. | 260/41 |
| 4,038,247 | 7/1977 | Muller et al. | 524/193 |
| 4,145,556 | 3/1979 | Hirsch et al. | 560/74 |
| 4,514,533 | 4/1985 | Hansen | 524/89 |
| 4,520,146 | 5/1985 | Hansen | 524/89 |
| 4,801,749 | 1/1989 | Kazmierczak et al. | 564/158 |
| 4,874,803 | 10/1989 | Baron et al. | 524/9.7 |

FOREIGN PATENT DOCUMENTS

3500058A1  7/1986  Fed. Rep. of Germany .

OTHER PUBLICATIONS

*Encyclopedia of Polymer Science and Engineering*, vol. 2, p. 75 (1985), John Wiley & Sons, New York, N.Y.
*Chemical Abstracts*, 82:113599z.
*Chemical Abstracts*, 86:1633625.

*Primary Examiner*—David B. Springer
*Attorney, Agent, or Firm*—Panitch Schwarze Jacobs & Nadel

[57] ABSTRACT

Phenolic N-(amido) imides are provided which are useful as antioxidant stabilizers for organic materials, including a large variety of synthetic polymers, typically subject to thermooxidative degradation. The antioxidant effectiveness of the phenolic N-(amido)imide stabilizers is enhanced by the deactivating potential of the amido-imide moiety towards metals or metal ions that frequently contaminate polymer compositions and serve to catalyze thermal degradation.

4 Claims, No Drawings

HINDERED PHENOLIC N-(AMIDO)IMIDES

BACKGROUND OF THE INVENTION

1. Field of The Invention

This invention relates to phenolic imides which are useful as antioxidant stabilizers for organic materials, including a large variety of synthetic polymers, typically subject to thermooxidative degradation. The antioxidant effectiveness of the stabilizers of the present invention is enhanced by the deactivating potential of the amido-imide moiety towards metals or metal ions that frequently contaminate polymer compositions and serve to catalyze thermal degradation.

2. Description of Prior Art

Degradation of a polymeric material, such as plastic, generally occurs when the polymeric material is exposed to a high temperature environment either during processing or in final application. This degradation is evidenced by discoloration, cracking and loss of mechanical properties of the polymeric material. To help prevent these degradative effects, a multitude of heat stabilizer additives are commercially available which can be added to the polymeric material. For example, polymeric materials may be protected against thermooxidative degradation by adding an antioxidant stabilizer to the polymeric material to inhibit or terminate free radical induced chain reactions. This type of stabilizer interrupts the propagation step in the oxidative degradation mechanism and thereby reduces the overall oxidation rate. An example of such an antioxidant stabilizer to be added to the polymeric material is a hindered phenol.

Transition metals, such as copper, iron, cobalt and manganese and ions thereof are generally known to accelerate the rate of oxidation by catalyzing the decomposition of hydroperoxides to radical species. See *Encyclopedia of Polymer Science and Engineering*, John Wiley & Sons, New York, N.Y., 1985, Vol. 2, p. 75. Therefore, a metal deactivator compound may be added to the polymeric material to inhibit thermal degradation. The metal deactivator generally forms complexes with the aforementioned metals or metal ions to block their catalytic activity. Oxamide and hydrazine derivatives are generally the types of compounds used as metal deactivators.

Coupling hindered phenols to metal deactivating moieties is generally an effective method for enhancing the thermooxidative stability of both polymeric and non-polymeric organic materials. This coupling strategy is well known in the art. For example, U.S. Pat. No. 3,706,798 of Dunnenberger and U.S. Pat. No. 3,734,884 of Biland disclose phenolic bisoxalic acid diamides as stabilizers for polypropylene.

U.S. Pat. No. 4,038,247 of Muller et al. discloses that phenolic diacyl dihydrazides are particularly effective for stabilizing polyolefins against metal catalyzed oxidation.

U.S. Pat. No. 4,145,556 of Hirsh et al. teaches the use of N,N'-bis[(alkylhydroxyphenyl)alkanoylhydrocarbyl]oxamides as stabilizers for polyolefins against degradation from thermal and metal catalyzed oxidation. Several commercial antioxidants contain similar chemical structures. For example, N,N'-bis(3,5-di-t-butyl-4-hydroxyhydrocinnamoyl)hydrazine is one such compound and is available from Ciba-Geigy. Another structurally similar compound is 2,2'-oxamidobisethyl(3,5-di-t-butyl-4-hydroxyhydrocinnamate), commercially available from Uniroyal.

Other hydrazine-type linkages that have been shown to be effective metal deactivators are N-(amido)imide linkage, prepared by reacting hydrazides with compounds containing a cyclic anhydride group. Yoshikawa et al. demonstrated the metal deactivating capability of such compounds in U.S. Pat. Nos. 3,933,736 and 3,956,332 by incorporating N-(salicyloylamino)imides into polyolefin compositions.

Hindered phenolic hydrazides have also been reacted with certain types of cyclic anhydrides to form N-(amido)imide antioxidant stabilizers. Hansen has coupled such hindered phenols to halogenated norbornene-2,3-dicarboxylic anhydrides (U.S. Pat. No. 4,514,533) and to halogenated phthalic anhydrides (U.S. Pat. No. 4,520,146) to obtain antioxidant/flame retardant additives.

Helwig et al. (German Offenlegungsschrift 3,500,058) have prepared other N-(amido)phthalimides from hindered phenolic hydrazides and substituted phthalic anhydrides as antioxidants for polypropylene. U.S. Pat. No. 4,874,803 of Baron et al. discloses preparing a series of bis N-(amido)imide antioxidants from bis-anhydride substrates as additives for a variety of polymers.

DEFINITIONS

As used herein, the terms "polymer" or "polymeric composition(s)" include homopolymers, any type of copolymers or any combinations, blends or alloys thereof.

As used herein, "%" or "percent" means the weight percent of the particular compound in the composition being described unless otherwise indicated or clear from the context of the description.

SUMMARY OF THE INVENTION

This invention is directed to a compound having the following Formula I:

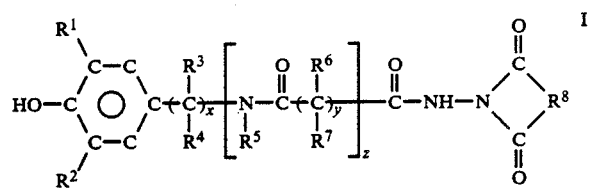

wherein
$R^1$ is t-alkyl of 4 to 8 carbons or cycloalkyl of 3 to 6 carbons;
$R^2$ is hydrogen, alkyl of 1 to 8 carbons, t-alkyl of 4 to 8 carbons or cycloalkyl of 3 to 6 carbons;
$R^3$ is hydrogen, lower alkyl of 1 to 6 carbons, phenyl or a phenol having the formula

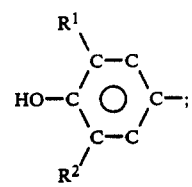

$R^4$, $R^5$, $R^6$ and $R^7$ are independently hydrogen, lower alkyl of 1 to 6 carbons or phenyl;

$R^8$ is a substituted or unsubstituted aliphatic diradical of 2 to 64 carbons, a substituted or unsubstituted alicyclic diradical of 3 to 12 carbons or a substituted or unsubstituted alibicyclic diradical of 5 to 18 carbons, with the proviso that the $R^8$ diradical has valence locants on adjacent carbons; wherein substituents for $R^8$ are alkyl of 1 to 24 carbons, alkoxy of 1 to 24 carbons, alkylthio of 1 to 24 carbons, alkenyl of 2 to 24 carbons, oxydialkyl of 2 to 24 carbons, thiodialkyl of 2 to 24 carbons, acyloxy of 2 to 24 carbons, alkoxycarbonyl of 2 to 24 carbons, cycloaliphatic of 3 to 12 carbons, dialkylaminocarbonyl of 3 to 41 carbons or phenyl;

x is an integer from 0 to 6;
y is an integer from 0 to 10; and
z is 0 or 1.

Another aspect of this invention relates to stabilizing a polymer against the degradative effects of thermooxidation by adding to the polymer an amount of a compound of Formula I effective to stabilize the polymer against the degradative effects of thermooxidation.

The novel antioxidant stabilizers of the present invention offer two modes of thermooxidative protection for organic substrate compositions. The chemical structure provides a primary or phenolic antioxidant which inhibits or terminates free radical induced chain reactions and an N-(amido)imide linkage to deactivate, by complexation, trace metal impurities known to catalyze thermooxidative degradation. The stabilizers of the present invention may be used to provide antioxidant protection to various organic compounds, such as engine lubricating oils and a variety of synthetic homopolymers, copolymers and polymer blends. The presently preferred use of the compounds of the present invention is as stabilizers for the polyolefin class of homopolymers, copolymers and polymer blends.

DETAILED DESCRIPTION OF THE PREFERRED EMBODIMENTS

As indicated above, the present invention relates to a novel phenolic N-(amido)imide stabilizer compound having the following Formula I:

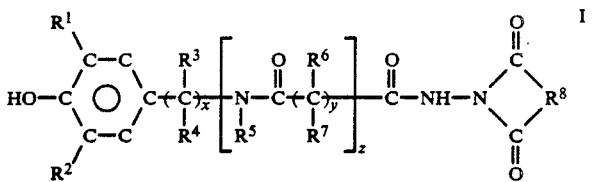

wherein
$R^1$, $R^2$, $R^3$, $R^4$, $R^5$, $R^6$, $R^7$, $R^8$, x, y and z are as previously defined.

Preferably, $R^1$ is t alkyl of 4 or 5 carbons and is more preferably t-butyl.

Preferably, $R^2$ is alkyl of 1 to 8 carbons or t-alkyl of 4 to 8 carbons and is more preferably t-butyl.

Preferably, $R^3$, $R^4$, $R^5$, $R^6$ and $R^7$ are independently hydrogen or alkyl of 1 to 8 carbons.

More preferably, $R^3$, $R^4$, $R^5$, $R^6$ and $R^7$ are hydrogen.

Preferably, $R^8$ is a substituted or unsubstituted aliphatic diradical of 2 to 24 carbons, a substituted or unsubstituted alicyclic diradical of 5 to 7 carbons or a substituted or unsubstituted alibicyclic diradical of 7 to 12 carbons; Wherein substituents for $R^8$ are alkyl of 1 to 16 carbons, alkoxy of 1 to 16 carbons, alkylthio of 1 to 16 carbons, alkenyl of 2 to 17 carbons, oxydialkyl of 2 to 17 carbons, thiodialkyl of 2 to 17 carbons, acyloxy of 2 to 17 carbons, alkoxycarbonyl of 2 to 17 carbons or cycloaliphatic of 5 to 8 carbons.

More preferably, $R^8$ is a substituted or unsubstituted aliphatic diradical of 2 to 20 carbons, a substituted or unsubstituted alicyclic diradical of 6 carbons or a substituted or unsubstituted alibicyclic diradical of 7 or 8 carbons; wherein substituents for $R^8$ are alkyl of 1 to 16 carbons, alkoxy of 1 to 16 carbons, alkylthio of 1 to 16 carbons, alkenyl of 2 to 17 carbons, oxydialkyl of 2 to 17 carbons, thiodialkyl of 2 to 17 carbons, acyloxy of 2 to 17 carbons, alkoxycarbonyl of 2 to 17 carbons or cycloaliphatic of 5 to 6 carbons.

Preferably, x is an integer from 0 to 4, y is an integer from 0 to 6 and z is 0 or 1.

More preferably, x is 3 and y and z are independently 0.

LIST OF ILLUSTRATIVE EXAMPLES

Non-limiting examples of presently preferred antioxidant imides of the present invention which may be used for stabilizing polymers against thermooxidative degradation include the following phenolic N-(amido)imides:

(1) N-[2-(3,5-di-t-butyl-4-hydroxyphenylamino)-2-oxoacetamido]-2-octadecylsuccinimide
(2) N-[3-(3,5-di-t-butyl-4-hydroxyphenyl)-propanamido]-2-octylsuccinimide
(3) N-[3-(3,5-di-t-butyl-4-hydroxyphenyl)-propanamido]-2-hexadecylsuccinimide
(4) N-[3-(3,5-di-t-butyl-4-hydroxyphenyl)-propanamido]-2-octadecylsuccinimide
(5) N-[3-(3,5-di-t-butyl-4-hydroxyphenyl)-propanamido]-5-norbornene-2,3-dicarboximide
(6) N-[3-(3,5-di-t-butyl-4-hydroxyphenyl)-propanamido]-2-isododecenylsuccinimide
(7) N-[4-(3,5-di-t-butyl-4-hydroxyphenylamino)-4-oxobutanamido]-2-octadecylsuccinimide
(8) N-[6-(3,5-di-t-butyl-4-hydroxyphenylamino)-6-oxohexanamido]-2-hexadecylsuccinimide
(9) N-{10-[3-(3,5-di-t-butyl-4-hydroxyphenyl)-propylamino]-10-oxodecanamido}-2-octylsuccinimide
(10) N-[2-(3-t-amyl-5-methyl-4-hydroxyphenylamino)-2-oxoacetamido]-2-hexadecylsuccinimide
(11) N-[3-(3,5-di-t-butyl-4-hydroxyphenyl)-propanamido]-4-methylhexahydrophthalimide
(12) N-[3,3-bis(3'-t-butyl-4'-hydroxyphenyl)-butanamido]-2-octadecylsuccinimide
(13) N-[3-(3,5-di-t-butyl-4-hydroxyphenyl)-propanamido]-2-dodecylsuccinimide
(14) N-[3-(3,5-di-t-butyl-4-hydroxyphenyl)-propanamido]methyl-5-norbornene-2,3-dicarboximide
(15) N-[3-(3,5-di-t-butyl-4-hydroxyphenyl)-propanamido]-4-octadecylthiohexahydrophthalimide
(16) N-[3-(3,5-di-t-butyl-4-hydroxyphenyl)-propanamido]dodecylmaleimide
(17) N-[3-(3,5-di-t-butyl-4-hydroxyphenyl)-propanamido]-2-tetradecylsuccinimide
(18) N-[3-(3,5-di-t-butyl-4-hydroxyphenyl)-propanamido]-2-(hexadecylthiomethyl)succinimide
(19) N-[3-(3,5-di-t-butyl-4-hydroxyphenyl)-propanamido]maleimide Other compounds within Formula I could be prepared by one skilled in the art based on the present disclosure.

PREPARATION OF COMPOUNDS OF THE PRESENT INVENTION

The antioxidant stabilizers of the present invention, designated generally as Formula I, may be prepared by reacting phenolic hydrazides with a substituted or unsubstituted succinic anhydride or a substituted or unsubstituted maleic anhydride. These phenolic N-(amido)imide stabilizers are formed in a two-step reaction where an intermediate amidic acid or amic acid is initially prepared by reacting the hydrazide functionality with the cyclic anhydride linkage. Under appropriate dehydrating conditions, the amidic or amic acid further reacts to yield the final phenolic N-(amido)imide stabilizer.

Preparative conditions can be adjusted such that the amidic acid or amic acid intermediate is not isolated and the reaction proceeds directly to the phenolic imide final product. The reaction is typically carried out in an inert solvent, such as dimethyl formamide (DMF), ethers, aliphatic hydrocarbons and aromatic hydrocarbons, such as toluene, xylene, dichlorobenzene or mesitylene, usually at solvent reflux temperatures. Imide formation can be further facilitated by the azeotropic removal of water during the reaction.

In some cases, the reaction for preparing the antioxidant stabilizers of the present invention may be conducted without a solvent. When the physical properties of the reactants and products permit, the reaction can be conducted as a melt that is heated, optionally under a vacuum, to yield the products directly. Temperatures used in the solventless or neat process may vary depending on the viscosity of the melt. Generally, a lower reaction temperature is permitted when the melt viscosity is low. In any event, the reaction temperatures are generally above the boiling point of water at any given pressure. Owing to these viscosity considerations, stirring and transferring the reaction mixtures and like processes generally require temperatures above 75° C. Temperatures of 150° C or higher may be necessary to obtain a fluid, workable reaction mixture.

The phenolic hydrazide precursors to the antioxidant stabilizers of the present invention may be illustrated by the following Formula II:

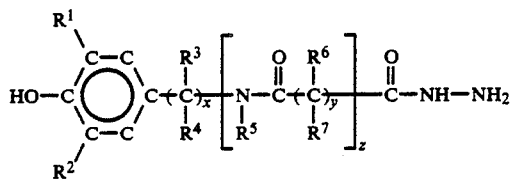

$R^1$, $R^2$, $R^3$, $R^4$, $R^5$, $R^6$, $R^7$, x, y and z are as previously defined.

The Formula II phenolic hydrazide starting materials are typically prepared by reacting an ester of an alkylhydroxyphenylalkanoic acid with hydrazine. More detailed explanations of the preparation of these types of phenolic hydrazides are well known to those skilled in the art and can be found in U.S. Pat. Nos. 3,888,824 and 4,801,749, the disclosures of which are hereby incorporated herein by reference.

Non-limiting examples of Formula II phenolic hydrazide precursors that are useful for preparing the Formula I stabilizers of the present invention include:

(1) 3,5-di-t-butyl-4-hydroxybenzoic acid hydrazide (2) 3-(3,5-di-t-butyl-4-hydroxyphenyl)propanoic acid hydrazide (3) 2-(3,5-di-t-butyl-4-hydroxyphenylamino)-2-oxoacetyl hydrazide (4) 2-(2-(3-t-amyl-5-methyl-4-hydroxyphenyl)-butylamino)-2-oxoacetyl hydrazide (5) 4-(3,5-di-t-butyl-4-hydroxyphenylamino)-4-oxobutanoyl hydrazide (6) 6-(3,5-di-t-butyl-4-hydroxyphenylamino)-6-oxohexanoyl hydrazide (7) 10-(3,5-di-t-butyl-4-hydroxyphenylamino)-10-oxodecanoyl hydrazide Other examples of useful phenolic hydrazides can be found in previously cited U.S. Pat. Nos. 3,888,824 and 4,801,749 incorporated herein by reference. Many other examples of this type of compound will generally be obvious to one skilled in the art. The examples given are illustrative and are not intended to limit the scope of the invention.

Cyclic anhydride substrates used to prepare the Formula I stabilizers of the present invention may be illustrated by the following Formula III:

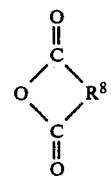

$R^8$ is as previously defined.

In the Formula I and Formula III compounds of the present invention, the $R^8$ diradical is defined as having valence locants on adjacent carbon atoms. Consequently, the bonds connecting the $R^8$ diradical to the two carbonyl carbons of the imide in Formula I and the bonds connecting the $R^8$ diradical to the two carbonyl carbons of the cyclic anhydride in Formula III are located on adjacent or alpha carbons in the $R^8$ diradical. In this manner, the Formula I imide ring and the Formula III anhydride ring are each 5-membered rings. In the event the $R^8$ diradical has more than two carbons, the remaining carbons generally may be viewed as substituents branching off from the Formula I imide ring or the Formula III anhydride ring.

The Formula III cyclic anhydride precursors are a class of compounds very well known in the art. Succinic anhydrides comprising carbocylic substituents can generally be prepared by the Diels-Alder reaction of dienes with maleic anhydride. Succinic anhydrides comprising unsaturated aliphatic substituents may be prepared by reacting maleic anhydride with olefins (See CA 82:113500z and 86:173372b). This latter process often affords isomeric mixtures of alkenyl succinic anyhydrides that require distillative fractionation for further purification. The fractions obtained by distillation are generally only somewhat less complex mixtures. However, the distillative fractions are generally largely free of residual maleic anhydride or olefin. Saturated analogs of these materials are subsequently prepared by hydrogenation. Many such substituted succinic anhydrides are commercially available.

Non-limiting examples of such Formula III cyclic anhydride substrates are as follows:

(1) 2-methylsuccinic anhydride
(2) 2-n-oct-2-enylsuccinic anhydride
(3) 2-n-octylsuccinic anhydride (4) 2-(4,6,8-trimethylnon-2-enyl)succinic anhydride
(5) 2-(4,6,8-trimethylnonyl)succinic anhydride
(6) 2-n-dodecylsuccinic anhydride
(7) 2-n-tetradecylsuccinic anhydride
(8) 2-n-octadecylsuccinic anhydride
(9) 2-n-dotriacontylsuccinic anhydride
(10) 2-n-hexacontylsuccinic anhydride
(11) 5-norbornene-2,3-dicarboxylic anhydride
(12) hexahydrophthalic anhydride
(13) 4-methylhexahydrophthalic anhydride
(14) 2-n-hexadecylsuccinic anhydride
(15) maleic anhydride Many other examples of this type of cyclic anhydride compound will be readily apparent to one skilled in the art. The examples given are illustrative and do not intend to limit the scope of the invention.

UTILITY

The novel antioxidant stabilizers of the present invention are very effective additives for stabilizing organic compounds, for example, organic fluids, such as engine lubricating oils. In addition, the compounds of the present invention may be used to stabilize various synthetic polymeric compositions which are normally subject to thermooxidative degradation. At times it may be beneficial to add extraneous additives which will act as synergists with the N-(amido)imide stabilizers of the present invention.

The amount of stabilizer used to stabilize the polymeric composition will depend on the particular polymer system to be stabilized, the degree of stabilization desired and the presence of other stabilizers in the composition. About 0.01% to about 10% by weight of an antioxidant stabilizer of this invention present in the polymeric composition provides suitable stabilization. A preferred range is from about 0.1% to about 3% by weight of the stabilizers in the final composition.

Non-limiting examples of polymeric compositions which may be stabilized by the novel stabilizer compounds of the present invention include:

(1) Polyolefins, such as high, low and linear low density polyethylenes, which may be optionally cross-linked, polypropylene, polyisobutylene, poly(methylbutene-1), polyacetylene and, in general, polyolefins derived from monomers having from two to about ten carbon atoms, and mixtures thereof.

(2) Polyolefins derived from diolefins, such as polybutadiene and polyisoprene.

(3) Copolymers of mono or diolefins, such as ethylene-propylene, propylene-butene-1, propylene-isobutylene and ethylene-butene-1 copolymer.

(4) Terpolymers of ethylene and propylene with dienes (EPDM), such as butadiene, hexadiene, dicyclopentadiene and ethylidene norbornene.

(5) Copolymers of alpha-olefins with acrylic acid or methacrylic acids or their derivatives, such as ethylene-acrylic acid, ethylene-methacrylic acid and ethylene-ethyl acrylate copolymers.

(6) Styrenic polymers, such as polystyrene (PS) and poly(p-methylstyrene).

(7) Styrenic copolymers and terpolymers, such as styrene-butadiene (SBR), styrene-allyl alcohol and styrene-acrylonitrile (SAN), styrene-acrylonitrile-methacrylate terpolymer, styrene-butadiene-styrene block copolymers (SBS), rubber modified styrenics, such as styrene-acrylonitrile copolymers modified with acrylic ester polymer (ASA), graft copolymers of styrene on rubbers, such as polybutadiene (HIPS), polyisoprene or styrene-butadiene-styrene block copolymers (Stereon TM products available from Firestone Synthetic Rubber and Latex Co.), graft copolymers of styrene-acrylonitrile on rubbers, such as butadiene (ABS), polyisoprene or styrene-butadiene-styrene block copolymers, graft copolymers of styrene-methyl methacrylate on rubbers, such as polybutadiene (MBS), butadiene-styrene radial block copolymers (e.g., KRO 3 TM of Phillips Petroleum Co.), selectively hydrogenated butadiene-styrene block copolymers (e.g., Kraton G TM from Shell Chemical Co.) and mixtures thereof.

(8) Polymers and copolymers derived from halogen-containing vinyl monomers, such as poly(vinyl chloride), poly(vinyl fluoride), poly(vinylidene chloride), poly(vinylidene fluoride), poly(tetrafluoroethylene) (PTFE), vinyl chloride-vinyl acetate copolymers, vinylidene chloride-vinyl acetate copolymers and ethylenetetrafluoroethylene copolymers.

(9) Halogenated rubbers, such as chlorinated and/or brominated butyl rubbers or polyolefins and fluoroelastomers.

(10) Polymers and copolymers derived from alpha,-beta-unsaturated acids, anhydrides, esters, amides and nitriles or combinations thereof, such as polymers or copolymers of acrylic and methacrylic acids, alkyl and-/or glycidyl acrylates and methacrylates, acrylamide and methacrylamide, acrylonitrile, maleic anhydride, maleimide, the various anhydride containing polymers and copolymers described in this disclosure, copolymers of the polymers set forth in this paragraph and various blends and mixtures thereof, as well as rubber modified versions of the polymers and copolymers set forth in this paragraph.

(11) Polymers and copolymers derived from unsaturated alcohols or their acylated derivatives, such as poly(vinyl alcohol), poly(vinyl acetate), poly(vinyl stearate), poly(vinyl benzoate), poly(vinyl maleate), poly(vinyl butyral), poly(allyl phthalate), poly(allyl diethylene glycol carbonate) (ADC), ethylene-vinyl acetate copolymer and ethylenevinyl alcohol copolymers.

(12) Polymers and copolymers derived from unsaturated amines, such as poly(allyl melamine).

(13) Polymers and copolymers derived from epoxides, such as polyethylene oxide, polypropylene oxide and copolymers thereof, as well as polymers derived from bis-glycidyl ethers.

(14) Poly(phenylene oxides), poly(phenylene ethers) and modifications thereof containing grafted polystyrene or rubbers, as well as their various blends with polystyrene, rubber modified polystyrene or nylon.

(15) Polycarbonates and especially the aromatic polycarbonates, such as those derived from phosgene and bisphenols such as bisphenol-A, tetrabromobisphenol-A and tetramethylbisphenol-A.

(16) Polyesters derived from dicarboxylic acids and diols and/or hydroxycarboxylic acids or their corresponding lactones, such as polyalkylene phthalates (e.g., polyethylene terephthalate (PET), polybutylene terephthalate (PBT) and poly (1,4-dimethylcyclohexane terephthalate) or copolymers thereof) and polylactones, such as polycaprolactone.

(17) Polyarylates derived from bisphenols (e.g., bisphenol-A) and various aromatic acids, such as isophthalic and terephthalic acids or mixtures thereof.

(18) Aromatic copolyester carbonates having carbonate as well as ester linkages present in the backbone of the polymers, such as those derived from bisphenols, iso- and terephthaloyl chlorides and phosgene.

(19) Polyurethanes and polyureas.

(20) Polyacetals, such as polyoxymethylenes and polyoxymethylenes which contain ethylene oxide as a comonomer.

(21) Polysulfones, polyethersulfones and polyimidesulfones.

(22) Polyamides and copolyamides which are derived from diamines and dicarboxylic acids and/or from aminocarboxylic acids or the corresponding lactones such as the following nylons: 6, 6/6, 6/10, 11 and 12.

(23) Polyimides, polyetherimides, polyamideimides and copolyetheresters.

(24) Cross-linked polymers which are derived from aldehydes on the one hand and from phenols, ureas and melamine on the other hand, such as phenol-formaldehyde, urea-formaldehyde and melamine-formaldehyde resins.

(25) Alkyl resins, such as glycerolphthalic acid resins and mixtures thereof with melamine-formaldehyde resins.

(26) Blends of vinyl monomers and unsaturated polyester resins which are derived from copolyesters of saturated and unsaturated dicarboxylic acids with polyhydric alcohols, as well as from vinyl compounds (crosslinking agents) and also halogen-containing, flame resistant modifications thereof.

(27) Natural polymers, such as cellulose and natural rubber, as well as the chemically modified homologous derivatives thereof, such as cellulose acetates, cellulose propionate, cellulose butyrate and the cellulose ethers, such as methyl and ethyl cellulose.

The novel N-(amido)imide antioxidant stabilizers of this invention can be used together with other additives to further enhance the properties of the finished polymer. Examples of other additives that can be used in conjunction with the antioxidant stabilizers of this invention include other antioxidants, such as alkylated monophenols, alkylated hydroquinones, hydroxylated thiodiphenyl ethers, alkylidene-bis-phenols, hindered phenolic benzyl compounds, acylaminophenols, esters of 3-(3,5-di-t-butyl-4-hydroxyphenyl)propionic acid, esters of 3-(5-t-butyl-4-hydroxy-3-methylphenyl)propionic acid, 3-(3,5-di-t-butyl-4-hydroxyphenyl)propionic acid amides; UV absorbers and light stabilizers, such as 2-(2'-hydroxyphenyl)-2H-benzotriazoles, 2-hydroxybenzophenones, benzylidene malonate esters, esters of substituted or unsubstituted benzoic acids, diphenyl acrylates, nickel chelates, oxalic acid diamides, hindered amine light stabilizers; metal alkanoates (e.g., calcium stearate) and metal deactivators; organo-phosphorous and organo-sulfur stabilizers, for example, organo-phosphites, organo-phosphonites and dialkythiopropionates; other additives, such as fillers and reinforcing agents, plasticizers, lubricants, corrosion and rust inhibitors, emulsifiers, mold release agents, pigments, carbon black, fluorescent brighteners, both organic and inorganic flame retardants and non-dripping agents, melt flow improvers and antistatic agents.

The effective amounts of these additives would be well known to those skilled in the art or could be determined readily without undue experimentation.

The following examples are presented to provide a more detailed explanation of the present invention and are intended as illustrations and not limitations of the invention.

EXAMPLES

Starting Materials

Octadecylsuccinic anhydride, hexadecylsuccinic anhydride, tetradecylsuccinic anhydride, octylsuccinic anhydride and isododecenylsuccinic anhydride, used in the following examples, are products of the Humphrey Chemical Co. 4-Methylhexahydrophthalic anhydride was obtained from Milliken Chemical. 5-Norbornene-2,3-dicarboxylic anhydride is a product of Eastman Chemical and methyl 5-norbornene-2,3-dicarboxylic anhydride is available from the Aldrich Chemical Co.

EXAMPLE 1

3,3'-Bis(3'-t-butyl-4'-hydroxyphenyl)butanoic acid hydrazide

Bis[3,3-bis(3'-t-butyl-4'-hydroxyphenyl)butanoic acid] glycol ester (Hostanox 03 ™, a product of American Hoechst Corp.) (15.0 g, 18.8 mmol) and 54% aqueous hydrazine (10.0 g, 168.5 mmol) were combined and refluxed for 7 hours under a nitrogen atmosphere. After cooling, the mixture was extracted with 130 ml of t-butyl methyl ether. The organic layer was washed successively with 50 ml portions of water and saturated NaCl solution, followed by drying over anhydrous sodium sulfate. After filtering off the drying agent, the organic solution was concentrated on a rotary evaporator and subsequently on a high vacuum system. A low melting (35° C. to 50° C.), white crystalline solid was obtained (16.5 g). Liquid chromatography indicated that the product contained small amounts of the starting glycol ester and residual solvent.

IR(CHCl$_3$): 3606 cm$^{-1}$ (OH); 3150 cm$^{-1}$–3450 cm$^{-1}$ (NH, diffuse); 1664 cm$^{-1}$, 1628 cm$^{-1}$ (C=O).

EXAMPLE 2

N-[3,3-bis(3'-t-butyl-4'-hydroxyphenyl)butanamido]-2-octadecylsuccinimide

The product of Example 1 (5.9 g, 13.7 mmol) and 2-octadecylsuccinic anhydride (4.8 g, 13.7 mmol) were combined in 65 ml of toluene. The mixture was stirred and refluxed for 1 hour under a nitrogen atmosphere with the azeotropic removal of water (Dean Stark Assembly). The mixture was cooled and the solvent was removed on a rotary evaporator. The mixture was placed under high vacuum for 20 minutes while warming the flask containing the mixture in a 50° C. water bath. A very light tan solid (9.5 g) was obtained having a melting range of 70°–75° C.

IR(CHCl$_3$): 3590 cm$^{-1}$ (OH); 1722 cm$^{-1}$ (C=O).

EXAMPLE 3

N-[2-(3,5-di-t-butyl-4-hydroxyphenylamino)-2-oxoacetamido]-2-octadecylsuccinimide 2-(3,5-di-t-butyl-4-hydroxyphenylamino)-2-oxoacetyl hydrazide, (prepared by the procedure set forth in U.S. Pat. No. 4,801,749) (2.6 g, 8.5 mmol), 2-octadecylsuccinic anhydride (3.2 g, 8.5 mmol) and 40 ml of toluene were combined and refluxed under a nitrogen atmosphere with the azeotropic removal of water for 45 minutes. The solvent was removed under vacuum. Last traces of solvent were removed by heating the mixture under high vacuum to about 120° C. Upon cooling to room temperature, 5.7 g of a light amber glass was obtained. The brittle glass was shattered and pulverized with a mortar and pestle to give a light yellow powder having a melting range of 40°–45° C.

IR (KBr): 3640 cm$^{-1}$ (OH); 1739 cm$^{-1}$, 1690 cm$^{-1}$, 1680 cm$^{-1}$ (C=O).

EXAMPLE 4

N-[3-(3,5-di-t-butyl-4-hydroxyphenyl)propanamido]-2-octadecylsuccinimide

2-Octadecylsuccinic anhydride (61.8 g, 161 mmol) was added to 150 ml of xylene. To this mixture was added 3-(3,5-di-t-butyl-4-hydroxyphenyl)propanoic acid hydrazide (47.1 g, 160 mmol). The mixture was refluxed for one hour under a nitrogen atmosphere with the azeotropic removal of water (Dean-Stark assembly). The bulk of the solvent was then distilled off and the mixture was cooled to about 110° C. A vacuum was applied and the temperature was increased to 150° C. to remove additional solvent. Cooling to 120° C., the vacuum was released and the resulting moderately viscous yellow liquid was poured into a shallow glass receiver. Upon cooling to room temperature, the liquid solidified to a clear yellow glass. The yellow glass was shattered and pulverized with a mortar and pestle to give 98.0 g of a light yellow powder having a melting point of about 32° C.

IR (KBr): 3640 cm$^{-1}$ (OH); 1735 cm$^{-1}$ (C=O).

EXAMPLE 5

N-[3-(3,5-di-t-butyl-4-hydroxyphenyl)propanamido]-2-hexadecylsuccinimide

2-Hexadecylsuccinic anhydride (10.5 g, 31.3 mmol), 3-(3,5-di-t-butyl-4-hydroxyphenyl)propanoic acid hydrazide (9.2 g, 31.3 mmol) and 10 ml of toluene were combined and refluxed for one hour under a nitrogen atmosphere with the azeotropic removal of water. Solvent was then removed under vacuum as the mixture was warmed to about 130° C. After 20 minutes, the reaction mixture was cooled and the vacuum was removed. The resulting viscous yellow mass was further chilled in an acetone/dry ice bath causing the mass to harden for facile removal from the reaction vessel. About 19 g of a viscous yellow gum was obtained that solidified to a translucent white solid upon standing for several days at room temperature.

IR (CHCl$_3$): 3640 cm$^{-1}$ (OH); 1730 cm$^{-1}$ (C=O).

EXAMPLE 6

N-[3-(3,5-di-t-butyl-4-hydroxyphenyl)propanamido]-2-hexadecylsuccinimide

2-Hexadecylsuccinic anhydride (10.5 g, 31.3 mmol) was heated to about 115° C. under a nitrogen atmosphere. To this stirred melt was added, in portions, 3-(3,5-di-t-butyl-4-hydroxyphenyl)propanoic acid hydrazide (9.2 g, 31.3 mmol). Successive additions of hydrazide required raising the melt temperature to facilitate stirring. The final addition of hydrazide was done at a melt temperature of approximately 135° C. After this final portion was blended into the melt, a vacuum was applied and the melt temperature was raised to about 148° C. and maintained at that temperature for 20 minutes. The melt was allowed to cool to approximately 115° C. whereupon the vacuum was released and the clear yellow melt was quickly poured into a container. 19.2 g of a yellow viscous liquid was obtained that solidified to a waxy, translucent white solid upon standing for several days at room temperature. The waxy material was recrystallized from acetone to give a white solid having a melting point of 85° C.

IR (CHCl$_3$): 3640 cm$^{-1}$ (OH); 1735 cm$^{-1}$ (C=O).

Elemental Anal.: Theoretical - C-74.09, H-10.28, N-4.85, O-10.79. Calc.: - C-74.20, H-10.43, N-4.68, O-10.69.

EXAMPLE 7

N-[3-(3,5-di-t-butyl-4-hydroxyphenyl)propanamido]-2-octylsuccinimide

A mixture of 3-(3,5-di-t-butyl-4-hydroxyphenyl)propanoic acid hydrazide (12.1 g, 41.1 mmol), 2-octylsuccinic anhydride (9.0 g, 41.1 mmol) and 20 ml of toluene was refluxed for one hour under a nitrogen atmosphere with the azeotropic removal of water (Dean-Stark assembly). The solvent was removed under vacuum while heating the reaction mass. 18.7 g of a very viscous, clear yellow liquid was obtained.

IR (film): 3640 cm$^{-1}$ (OH); 1735 cm$^{-1}$ (C=O).

EXAMPLE 8

N-[3-(3,5-di-t-butyl-4-hydroxyphenyl)propanamido]-2-isododecenylsuccinimide

A mixture of 2-isododecenylsuccinic anhydride (31.2 g, 111 mmol), 3-(3,5-di-t-butyl-4-hydroxy-phenyl)propanoic acid hydrazide (32.6 g, 111 mmol) and 60 ml of toluene was refluxed for 90 minutes under a nitrogen atmosphere with the azeotropic removal of water (Dean-Stark assembly). The bulk of the solvent was distilled off followed by vacuum stripping of the hot (135° C.) melt for 25 minutes to remove last traces of solvent. After cooling to room temperature, the vacuum was removed. Additional cooling in an acetone/dry ice bath allowed for easy removal of the thermally fractured solid from the vessel. 61.7 g of an amber solid was obtained having a melting range of 62°–68° C.

IR (CHCl$_3$): 3640 cm$^{-1}$ (OH); 1730 cm$^{-1}$ (C=O).

EXAMPLE 9

N-[3-(3,5-di-t-butyl-4-hydroxyphenyl)propanamido]-5-norbornene-2,3-dicarboximide A mixture of 5-norbornene-2,3-dicarboxylic acid anhydride (7.6 g, 45.6 mmol), 3-(3,5-di-t-butyl-4-hydroxyphenyl)propanoic acid hydrazide (13.2 g, 44.7 mmol) and 280 ml of xylene was refluxed for one hour under a nitrogen atmosphere with the azeotropic removal of water (Dean-Stark assembly). Approximately 220 ml of solvent was distilled off and the mixture solidified after cooling to room temperature. This residue was slurried with 150 ml of pentane and the resulting solid material was collected by vacuum filtration and air dried. 19.3 g of a white crystalline solid was obtained having a melting point of 217° C.

IR (KBr): 3600 cm$^{-1}$ (OH); 1730 cm$^{-1}$, 1685 cm$^{-1}$ (C=O).

EXAMPLE 10

N-[3-(3,5-di-t-butyl-4-hydroxyphenyl)propanamido]-methyl-5-norbornene-2,3-dicarboximide In the manner of example 9, methyl-5-norbornene-2,3-dicarboxylic anhydride (83 g, 44.4 mmol), 3-(3,5-di-t-butyl-4-hydroxyphenyl)propanoic acid hydrazide (13.0 g, 44.2 mmol) and 150 ml of xylene were reacted to yield approximately 20.0 g of a white crystalline solid having a melting range of 195°–200° C.

IR (KBr): 3630 cm$^{-1}$ (OH); 1730 cm$^{-1}$, 1680 cm$^{-1}$ (C=O).

EXAMPLE 11

N-[3-(3,5-di-t-butyl-4-hydroxyphenyl)propanamido]-4-methylhexahydrophthalimide

A mixture of 4-methylhexahydrophthalic anhydride (32.8 g, 200 mmol), 3-(3,5-di-t-butyl-4-hydroxyphenyl)-propanoic acid hydrazide (58.4 g, 200 mmol) and 650 ml of xylene was refluxed for 90 minutes under a nitrogen atmosphere with the azeotropic removal of water. The solvent was removed on a rotary evaporator to afford approximately 89 g of a white solid having a melting range of 87°–92° C.

IR (Xylene): 3640 cm$^{-1}$ (OH); 1735 cm$^{-1}$ (C=O).

EXAMPLE 12

N-[3-(3,5-di-t-butyl-4-hydroxyphenyl)propanamido]-2-dodecylsuccinimide

A mixture of 2-dodecylsuccinic anhydride (42.17 g, 147.4 mmol), 3-(3,5-di-t-butyl-4-hydroxyphenyl)-propanoic acid hydrazide (43.31 g, 147.4 mmol) and 70 ml of toluene was refluxed for one hour under a nitrogen atmosphere with the azeotropic removal of water (Dean-Stark assembly). The bulk of the solvent was distilled off followed by vacuum stripping of the hot (160° C.) melt for about 10 minutes. The resulting yellow liquid was then cooled under vacuum to about 120° C. The vacuum was released and the melt was quickly poured into a container. Upon cooling, the liquid became a clear yellow glass. The product was recrystallized from acetone/water at ice bath temperatures to afford, after drying, a nearly quantitative recovery of the product as a white powder having a melting range of 55°–60° C.

IR(CHCl$_3$): 3640 cm$^{-1}$ (OH); 1737 cm$^{-1}$ (C=O).

EXAMPLE 13

N-[3-(3,5-di-t-butyl-4-hydroxyphenyl)propanamido]-2-tetradecylsuccinimide

A mixture of 2-tetradecylsuccinic anhydride (17.2 g, 52.5 mmol), 3-(3,5-di-t-butyl-4-hydroxyphenyl)-propanoic acid hydrazide (15.4 g, 52.5 mmol) and 40 ml of toluene was refluxed for about one hour under a nitrogen atmosphere with the azeotropic removal of water. The bulk of the solvent was then allowed to distill off. Residual solvent was removed by placing the heated mixture (140° C.) under vacuum for 15 minutes. The bath used to heat the mixture was cooled to 70° C. and the vacuum was released. The resulting viscous melt was dissolved in 120 ml of acetone and suction filtered to remove mechanical impurities. The filtrate was diluted to 700 ml with acetone. This solution was cooled in an ice/water bath to precipitate the product which was collected by vacuum filtration. The filtrate was then re-cooled in a −20° C. acetone/dry ice bath to obtain additional product which was also collected by filtration. The collected solids were combined, air dried on a sheet of paper and finally high vacuum dried to give 25.3 g of a white solid having a melting range of 70°–77° C.

IR(KBr): 3645 cm$^{-1}$ (OH); 1732 cm$^{-1}$, 1680 cm$^{-1}$ (C=O).

EXAMPLE 14

N-[3-(3,5-di-t-butyl-4-hydroxyphenyl)propanamido]-maleimide

A mixture of maleic anhydride (4.9 g, 50.0 mmol), 3-(3,5-di-t-butyl-4-hydroxyphenyl)propanoic acid hydrazide (15.2 g, 50.0 mmol) and 250 ml of xylene was refluxed for one hour under a nitrogen atmosphere with the azeotropic removal of water. The solvent was then removed on a rotary evaporator. The residual mass was extracted with 100 ml of tetrahydrofuran and the extract was added to 500 ml of hexane to precipitate the product. The product was collected by filtration and air dried. 16.1 g of a solid material was obtained having a melting range of 90°–94° C.

IR (xylene): 3640 cm$^{-1}$ (OH); 1740 cm$^{-1}$ (C=O).

EXAMPLE 15

This example illustrates the usefulness of the compounds of the present invention in stabilizing polypropylene. Also shown is the beneficial effect observed by using the compounds of the present invention in conjunction with costabilizers. The specific compounds used in this example are identified by the number of one of the above examples which describes the preparation of the compound.

The stabilizers were incorporated into Himont Pro-Fax ™ 6501 polypropylene resin using a C.W. Brabender type 125-25 H.C.V. extruder whose zone temperatures varied between 200° C. and 220° C. The extrudate was pelletized concurrently with the compounding operation. Prepared compositions were injection molded into 0.125" thick tensile bars using a Newbury 25 ton molding unit. Specimens were placed into a forced air oven at 150° C. and the number of hours to failure was noted. When the majority of specimens of a particular composition exhibited cracking, crazing or powdering, the composition was considered to have failed. Results of this evaluation can be found in Table I.

TABLE 1

| Stabilizer/Co-Stabilizer | Conc.(Wt. %) | Hours to Failure |
|---|---|---|
| None | — | 22 |
| Example 4 | 0.23 | 406 |
| Example 4/Irgafos 168* | 0.23/0.10 | 500 |
| Example 4/SAO+ | 0.23/0.10 | 625 |
| Example 6/Irgafos 168* | 0.21/0.10 | 500 |
| Example 6/SAO+/ Calcium Stearate | 0.21/0.10/0.10 | 750 |
| Example 6/SAO+/ Irgafos 168* | 0.21/0.10/0.05 | 850 |

*Tris (2,4-di-t-butylphenyl)phosphite; product of Ciba Geigy Corp.
+Isomeric mixture of beta-(n-octadecylthio)ethyl-3-(n-octadecylthio)cyclohexane and beta-(n-octadecylthio)ethyl-4-(n-octadecylthio)cyclohexane; product of Atochem North America, Inc.

EXAMPLE 16

Polypropylene stabilized with the compound of Example 4 was also heat aged at the lower oven temperature of 140° C. Markedly longer lifetimes of the composition resulted. The comparative data is presented in Table 2.

TABLE 2

| | | Hours to Failure | |
|---|---|---|---|
| Stabilizer/Co-Stabilizer | Conc.(Wt. %) | 140° C. | 150° C. |
| Example 4/Irgafos 168 | 0.23/0.10 | >3045* | 500 |

TABLE 2-continued

| Stabilizer/Co-Stabilizer | Conc.(Wt. %) | Hours to Failure | |
|---|---|---|---|
| | | 140° C. | 150° C. |
| Example 4/SAO | 0.23/0.10 | >3045* | 625 |

*Oven evalution discontinued prior to sample failure.

The present invention may be embodied in other specific forms without departing from the spirit or essential attributes thereof and, accordingly, reference should be made to the appended claims, rather than to the foregoing specification as indicating the scope of the invention.

I claim:

1. A compound having the following Formula I:

$$\text{HO}-\underset{R^2}{\underset{|}{C}}\underset{\diagdown}{\overset{R^1}{\diagup}}\underset{\diagup}{\overset{C-C}{\diagdown}}\underset{C-C}{\bigcirc}C\underset{R^4}{\underset{|}{(C)_x}}\underset{R^5}{\underset{|}{\left[\overset{O}{\overset{\|}{N}}-\overset{}{C}\underset{R^7}{\underset{|}{(C)_y}}\right]_z}}\overset{O}{\overset{\|}{C}}-\text{NH}-\text{N}\overset{\overset{O}{\overset{\|}{C}}}{\underset{\underset{O}{\overset{\|}{C}}}{\diamondsuit}}R^8 \quad \text{I}$$

wherein

R¹ is t-alkyl of 4 to 8 carbons or cycloalkyl of 3 to 6 carbons;

R² is hydrogen, alkyl of 1 to 8 carbons, t-alkyl of 4 to 8 carbons or cycloalkyl of 3 to 6 carbons;

R³ is hydrogen, lower alkyl of 1 to 6 carbons, phenyl or a phenol having the formula $$\text{HO}-\underset{R^2}{\underset{|}{C}}\underset{\diagdown}{\overset{R^1}{\diagup}}\underset{\diagup}{\overset{C-C}{\diagdown}}\underset{C-C}{\bigcirc}C-;$$

R⁴, R⁵, R⁶ and R7 are independently hydrogen, lower alkyl of 1 to 6 carbons or phenyl;

R⁸ is a substituted or unsubstituted aliphatic diradical of 2 to 64 carbons, a substituted or unsubstituted alicyclic diradical of 3 to 12 carbons or a substituted or unsubstituted alibicyclic diradical of 5 to 18 carbons, with the proviso that the R⁸ diradical has valence locants on adjacent carbons; wherein substituents for R⁸ are alkyl of 1 to 24 carbons, alkoxy of 1 to 24 carbons, alkylthio of 1 to 24 carbons, alkenyl of 2 to 24 carbons, oxydialkyl of 2 to 24 carbons, thiodialkyl of 2 to 24 carbons, acyloxy of 2 to 24 carbons, alkoxycarbonyl of 2 to 24 carbons, cycloaliphatic of 3 to 12 carbons, dialkylaminocarbonyl of 3 to 41 carbons or phenyl;

x is an integer from 0 to 6;

y is an integer from 0 to 10; and z is 0 or 1.

2. The compound according to claim 1 wherein

R¹ is t-alkyl of 4 or 5 carbons;

R² is hydrogen, alkyl of 1 to 8 carbons or t-alkyl of 4 or 5 carbons;

R³ is hydrogen, lower alkyl of 1 to 5 carbons or a phenol having the formula $$\text{HO}-\underset{R^2}{\underset{|}{C}}\underset{\diagdown}{\overset{R^1}{\diagup}}\underset{\diagup}{\overset{C-C}{\diagdown}}\underset{C-C}{\bigcirc}C-;$$

R⁴, R⁵, R⁶ and R7 are independently hydrogen or lower alkyl of 1 to 5 carbons;

R⁸ is a substituted or unsubstituted aliphatic diradical of 2 to 24 carbons, a substituted or unsubstituted alicyclic diradical of 5 to 7 carbons or a substituted or unsubstituted alibicyclic diradical of 7 to 12 carbons, wherein substituents for R⁸ are alkyl of 1 to 16 carbons, alkoxy of 1 to 16 carbons, alkylthio of 1 to 16 carbons, alkenyl of 2 to 17 carbons, oxydialkyl of 2 to 17 carbons, thiodialkyl of 2 to 17 carbons, acyloxy of 2 to 17 carbons, alkoxycarbonyl of 2 to 17 carbons or cycloaliphatic of 5 to 8 carbons;

x is an integer from 0 to 4; and y is an integer from 0 to 6.

3. The compound according to claim 2 wherein

R¹ is t-butyl;

R² is hydrogen, alkyl of 1 to 4 carbons or t-butyl;

R³ is hydrogen or a phenol having the formula $$\text{HO}-\underset{R^2}{\underset{|}{C}}\underset{\diagdown}{\overset{R^1}{\diagup}}\underset{\diagup}{\overset{C-C}{\diagdown}}\underset{C-C}{\bigcirc}C-;$$

R⁴, R⁵, R⁶ and R7 are independently hydrogen or methyl;

R⁸ is a substituted or unsubstituted aliphatic diradical of 2 to 20 carbons, a substituted or unsubstituted alicyclic diradical of 6 carbons or a substituted or unsubstituted alibicyclic diradical or 7 or 8 carbons, wherein substituents for R⁸ are alkyl of 1 to 16 carbons, alkoxy of 1 to 16 carbons, alkylthio of 1 to 16 carbons, alkenyl of 2 to 17 carbons, oxydialkyl of 2 to 17 carbons, thiodialkyl of 2 to 17 carbons, acyloxy of 2 to 17 carbons, alkoxycarbonyl of 2 to 17 carbons or cycloaliphatic of 5 to 6 carbons;

x is 3; and y and z are 0.

4. The compound according to claim 1 wherein the compound is selected from the group consisting of:

N-[3-(3,5-di-t-butyl-4-hydroxyphenyl)propanamido]-2-octadecylsuccinimide,

N-[3-(3,5-di-t-butyl-4-hydroxyphenyl)propanamido]-2-hexadecylsuccinimide,

N-[3-(3,5-di-t-butyl-4-hydroxyphenyl)propanamido]-2-dodecylsuccinimide,

N-[3-(3,5-di-t-butyl-4-hydroxyphenyl)propanamido]-2-octylsuccinimide,

N-[3,3-bis(3'-t-butyl-4'-hydroxyphenyl)butanamido]-2-octadecylsuccinimide,

N-[2-(3,5-di-t-butyl-4-hydroxyphenylamino)-2-oxoacetamido]-2-octadecylsuccinimide, N-[3-(3,5-di-t-butyl-4-hydroxyphenyl)propanamido]-2-isododecenylsuccinimide, N-[3-(3,5-di-t-butyl-4-hydroxyphenyl)propanimido]-5-norbornene-2,3-dicarboximide, N-[3-(3,5-di-t-butyl-4-hydroxyphenyl)propanamido]-methyl-5-norbornene-2,3-dicarboximide, N-[3-(3,5-di-t-butyl-4-hydroxyphenyl)propanamido]-4-methylhexahydrophthalimide, N-[3-(3,5-di-t-butyl-4-hydroxyphenyl)propanamido]-2-tetradecylsuccinimide and N-[3-(3,5-di-t-butyl-4-hydroxyphenyl)propanmido]-maleimide.

* * * * *